United States Patent [19]

Goldman

[11] Patent Number: 5,175,003
[45] Date of Patent: Dec. 29, 1992

[54] DUAL MECHANISM CONTROLLED RELEASE SYSTEM FOR DRUG DOSAGE FORMS

[75] Inventor: Robert Goldman, Cresskill, N.J.
[73] Assignee: Biosytes USA, Inc., Cresskill, N.J.
[21] Appl. No.: 505,723
[22] Filed: Apr. 6, 1990
[51] Int. Cl.⁵ ............................................. A61K 9/14
[52] U.S. Cl. ................................. 424/484; 424/480; 424/481; 424/482; 424/468
[58] Field of Search ............... 424/481, 482, 480, 468, 424/484

[56] References Cited

U.S. PATENT DOCUMENTS

| | | | |
|---|---|---|---|
| 3,043,747 | 7/1962 | Long | 424/481 |
| 4,155,993 | 5/1979 | Belleville | 424/482 |
| 4,432,966 | 2/1984 | Zeitoun | 424/482 |
| 4,606,909 | 8/1986 | Bechgaard | 424/482 |
| 4,704,285 | 11/1987 | Alderman | 424/480 |
| 4,772,475 | 9/1988 | Fukui | 424/482 |
| 4,775,536 | 10/1988 | Patell | 424/480 |
| 4,784,858 | 11/1988 | Ventouras | 424/482 |
| 4,786,506 | 11/1988 | Fontanelli | 424/481 |
| 4,816,264 | 3/1989 | Phillips | 424/468 |
| 4,859,471 | 8/1989 | Fülberth | 424/481 |
| 4,919,938 | 4/1990 | Lovegrove | 424/480 |

Primary Examiner—Thurman K. Page
Assistant Examiner—William E. Benston, Jr.
Attorney, Agent, or Firm—Klauber & Jackson

[57] ABSTRACT

A dual mechanism polymer mixture composed of pH-sensitive enteric materials and film-forming plasticizers capable of conferring permeability to the enteric material, for use in drug-delivery systems; a matrix pellet composed of a dual mechanism polymer mixture permeated with drug and sometimes covering a pharmaceutically neutral nucleus; a membrane-coated pellet comprising a matrix pellet coated with a dual mechanism polymer mixture envelope of the same or different composition; and a pharmaceutical dosage form containing matrix pellets. The matrix pellet releases acid-soluble drugs by diffusion in acid pH and by disintegration at pH levels of nominally about 5.0 or higher.

25 Claims, 3 Drawing Sheets

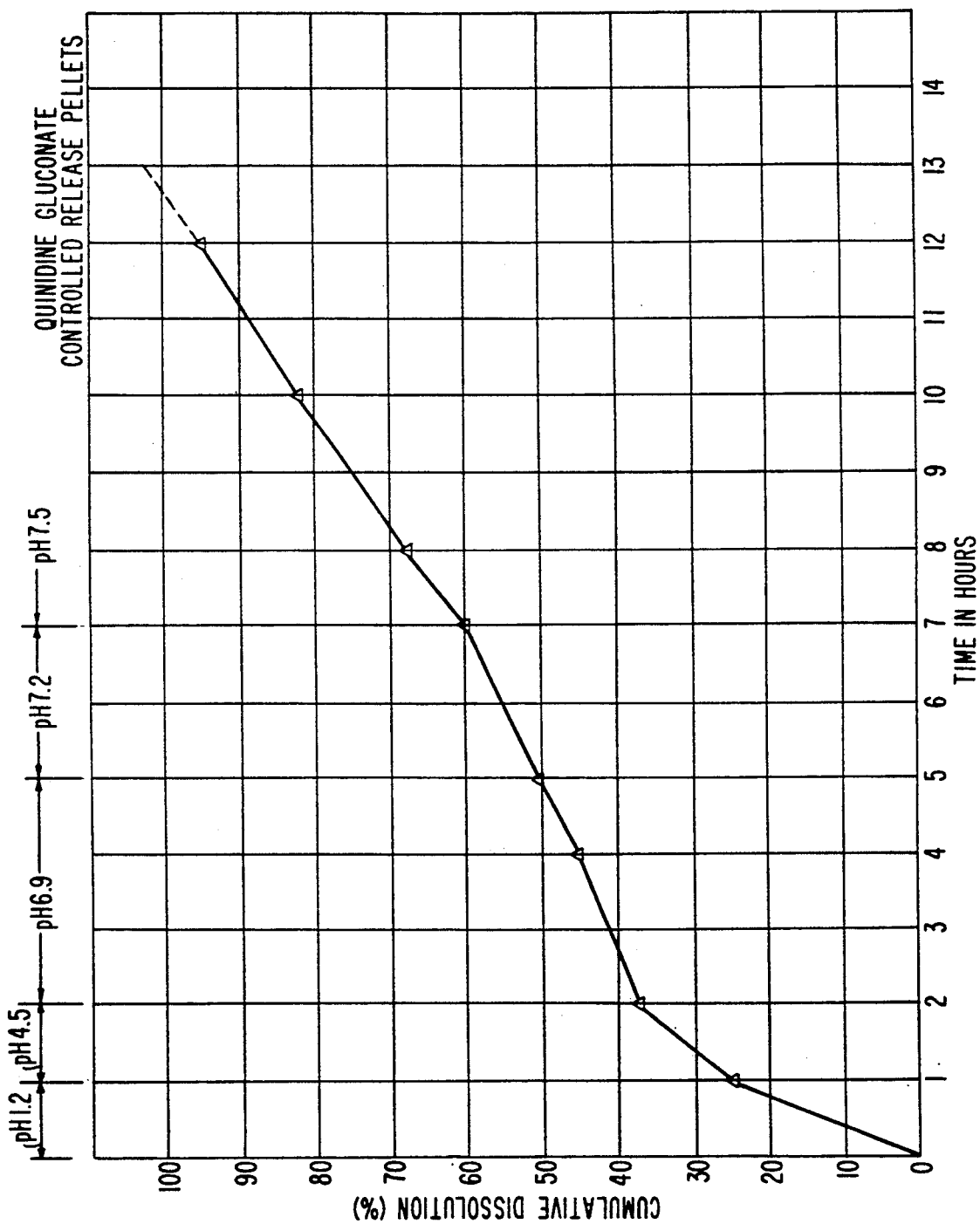

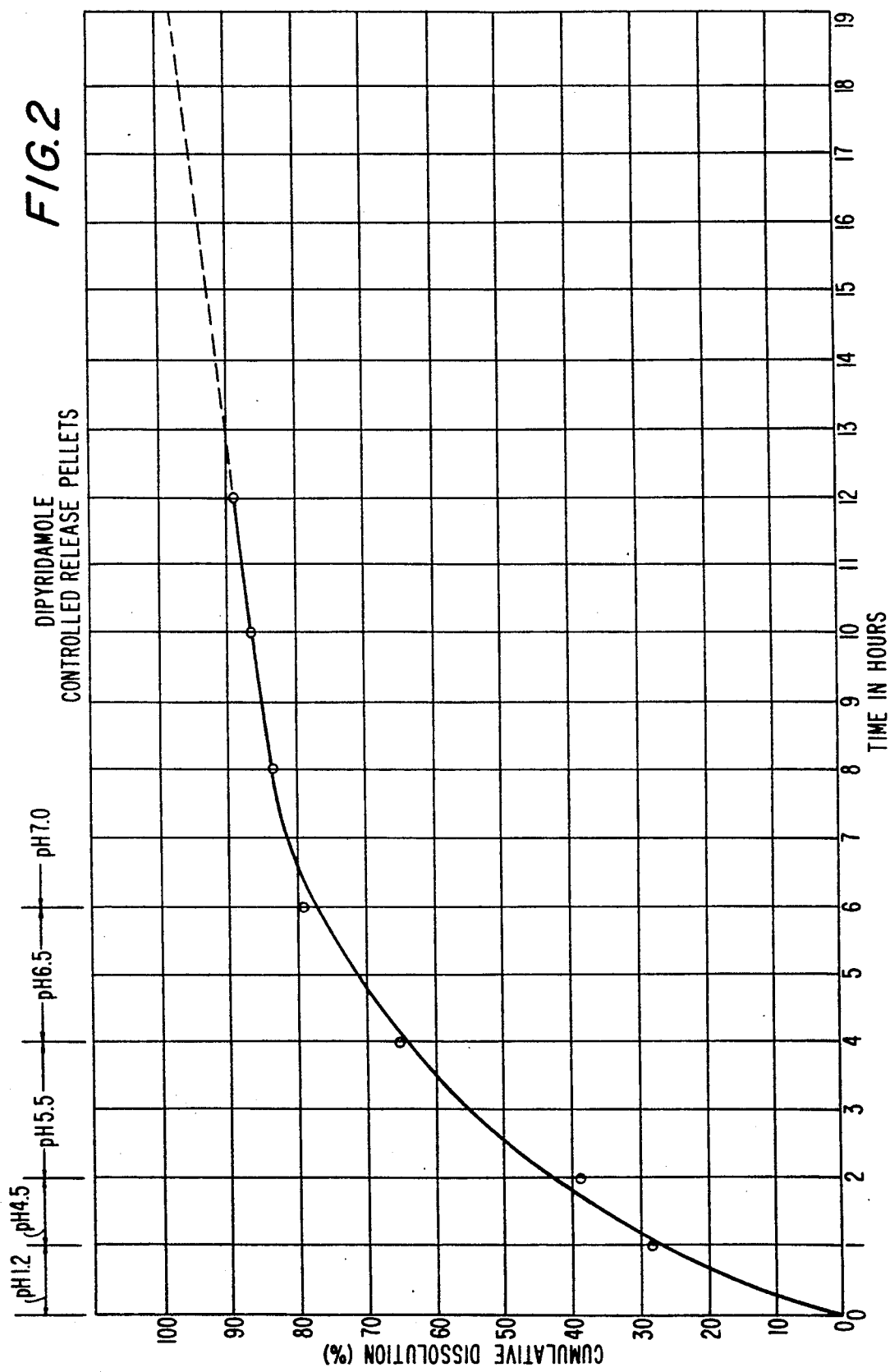

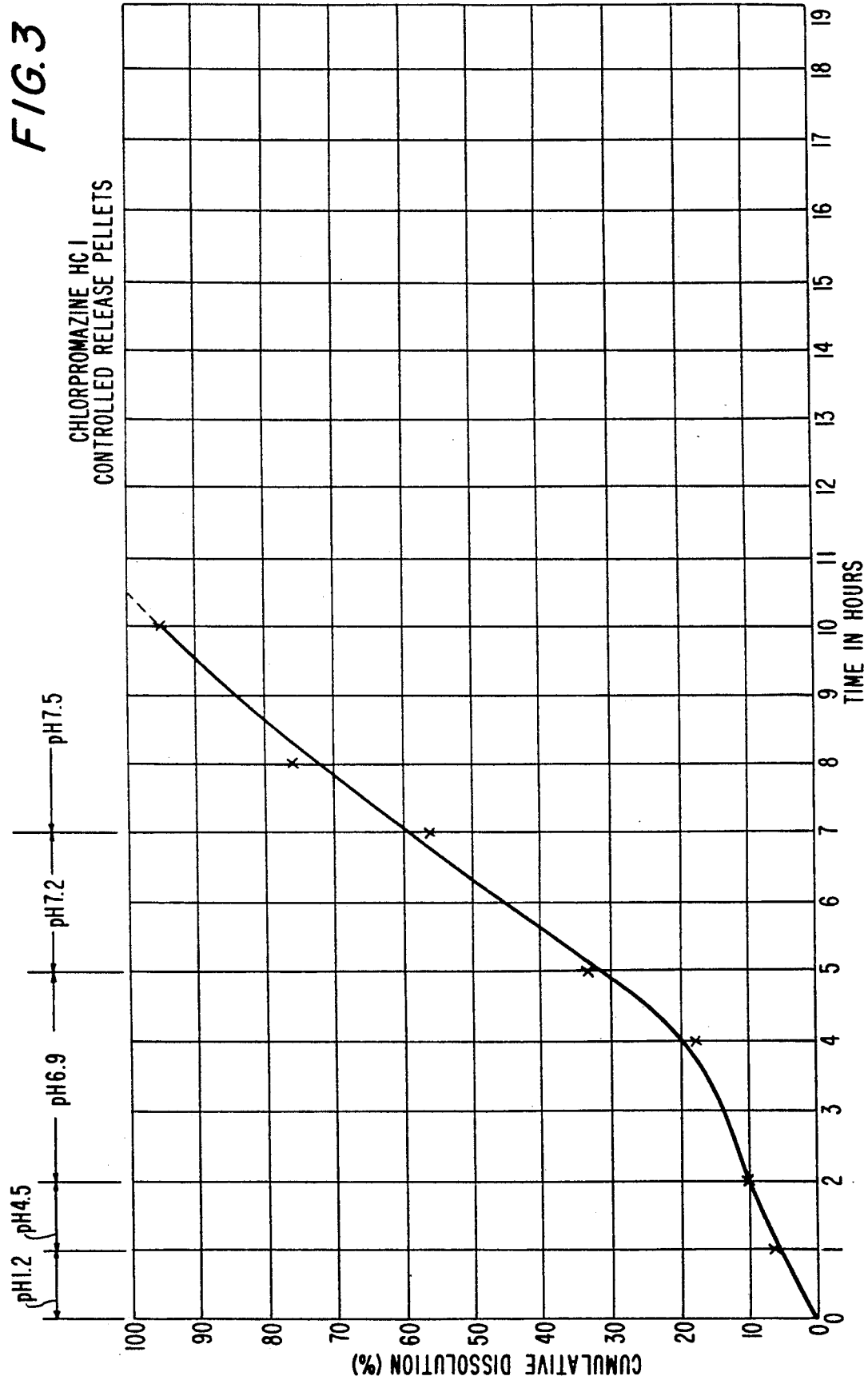

DUAL MECHANISM CONTROLLED RELEASE SYSTEM FOR DRUG DOSAGE FORMS

BACKGROUND OF THE INVENTION

1. Technical Field of the Invention

This invention relates to controlled release drug dosage forms. More particularly it relates to a controlled release dosage form wherein the drug is released by diffusion in an acid pH environment and by disintegration in an environment of higher pH.

2. The Prior Art

The preparation of drugs for oral administration in specialized dosage forms known variously as controlled delivery systems, sustained release, timed disintegration, etc., is widely used. One of the most advantageous, for many reasons, is the 2-piece hard gelatin capsule filled with drug in the form of a multiplicity of pellets so prepared that they release the drug for absorption by a diffusion process. A variation is the inclusion of such pellets in compressed tablets.

This type of formulation is limited to drugs which are sufficiently water soluble. Many commonly used drugs which could be, and in fact are, used in this way have sufficient water solubility or are water soluble salts of amines or other molecules which can form soluble salts with acidic materials. However, as they move down the gastrointestinal tract, with rising pH they are converted to the free amines. These amines in many cases may still be sufficiently water soluble to continue to be released from the pellets by a diffusion process.

Where a drug is of a water insoluble type, pellets having a disintegration release mechanism may be formulated. The disintegration mechanism may be actuated by, for example, pH changes or enzymatic activity or both in the gastrointestinal tract.

However, a problem comes about for certain drugs, typically amine salts which are water soluble and remain water soluble in the acidic gastric fluid to which they are first exposed after ingestion. Alternatively, they may be capable of forming water soluble salts in the acidic gastric fluid. But as they move down the gastrointestinal tract and encounter higher pH fluids they revert to very sparingly soluble, or practically water insoluble, form. In any event the water solubility of the free base is so low it is then inadequate for a diffusion rate controlled release process.

The mobility of both the hydrogen and hydroxyl ions are so much greater than that of the larger drug molecules, that dialytic membranes which are barriers to these larger drug molecules and which are suitable for reducing the transmission of these molecules to useable rates, are practically no barrier at all to the hydrogen or hydroxyl ion. The pH of the interior of the pellet therefore becomes very quickly the same as that of the digestive fluid in which it is immersed. This means that it does not matter whether the formulator starts with an amine salt or a free amine. The digestive fluid pH will determine whether it remains in soluble salt form, or is converted to the soluble salt form when in acidic gastric fluid. Similarly, the drug will revert to its sparingly soluble free amine form as the pellet moves down the gastrointestinal tract to regions of higher pH.

A typical example of such behavior is the cardiac antiarrhythmic drug quinidine. It is usually used in the form of one of its water soluble salts such as the gluconate or the sulfate. These salts are readily water soluble. However, the gluconate for example, which has a solubility of about 140 mg/ml of water at 25° C., falls to about 2 mg/ml at pH 7.5, and at pH 8.0, which may also be possible in the gastrointestinal tract, the solubility falls even lower, to about 0.4 mg/ml. All attempts to use a pure diffusion system have failed to produce a useful product. When the salt is converted to the free base the release process, for all practical purposes, stops. The total amount of drug that becomes available to the body for absorption under these conditions is erratic and rarely exceeds 50% of that present in the dosage form.

Another illustration of this type of problem is the cardiac drug dipyridamole. This is readily soluble in acid solutions. Pellets containing this drug and covered by a retarding dialytic membrane of satisfactory permeability for the drug, readily permit the passage of hydrogen ion to form a water soluble salt of the dipyridamole. But here again, further along in the gastrointestinal tract at higher pH values the release by diffusion ceases. Even if all of the original dipyridamole had been converted initially by gastric acidity to a soluble salt it would later revert to its free base. This inadequately soluble form will not diffuse at a useful rate through the retarding dialytic membrane which was of adequate permeability for the water soluble form of the drug.

It would be very useful to have a controlled release dosage form which could release drugs throughout the entire pH range found in the gastrointestinal tract because some drugs change markedly in solubility with pH. They are soluble in acidic media but only sparingly soluble, or practically insoluble, at higher pH values. This invention relates to such a controlled release system.

SUMMARY OF THE INVENTION

A polymer mixture is composed of pH-sensitive enteric materials and accessory materials which have both film-forming and plasticizing properties and which also render the enteric material permeable to drugs. When impregnated with a drug during manufacture, the dual mechanism polymer materials can form drug-containing matrix pellets. The matrix may cover a pharmaceutically-neutral nucleus which acts as a base or framework. A dual mechanism polymer membrane envelope, which may itself be impregnated with a drug, may cover the matrix pellet as part of the dual mechanism pellet. The dual mechanism pellet combines the properties of two distinct drug delivery systems: It releases acid-soluble drugs by diffusion in an acidic pH environment and by disintegration in an environment of nominally about pH 5.0 or higher. By manipulating the composition of the dual mechanism polymer membrane envelope and the drug-containing polymer matrix pellet independently, the rate of diffusion and of disintegration can be controlled. The drug-containing matrix pellets with or without a polymer membrane envelope, which envelope may contain a drug, forms a pharmaceutically acceptable dosage form.

BRIEF DESCRIPTION OF THE DRAWINGS

FIG. 1 is a graph showing the in vitro release of quinidine gluconate from dual mechanism polymer mixture controlled release pellets in accordance with the present invention;

FIG. 2 is a graph showing the in vitro release of dipyridamole from dual mechanism polymer mixture controlled release pellets in accordance with the present invention;

FIG. 3 is a graph showing the in vitro release of chlorpromazine HCl from dual mechanism polymer mixture controlled release pellets in accordance with the present invention.

DETAILED DESCRIPTION OF THE INVENTION

A. The Materials Used for the Dual Mechanism Polymer Mixture

Dual mechanism controlled release pellets are so called because they possess both the controllable dialytic properties necessary for drug diffusion and the pH sensitivity necessary for disintegration. Traditional dialytic materials used for diffusion pellets include shellac, ethyl cellulose and acrylic and methacrylic acid ester polymers marketed by Rohm and Haas under the trade names Eudragit RL and Eudragit RS. The prior art has suggested construction of hybrid forms of membranes or matrices by adding pH-sensitive materials to these dialytic materials. However, this approach failed to produce a useful polymer mixture or pellet. Applicant has discovered that this problem may be solved by starting with any of the commonly used pH-sensitive materials and conferring upon it dialytic properties as well. This solution to the problem is contrary to the approach heretofore suggested by the prior art and is, in fact, exactly opposite to that approach. As will be explained in more detail below, the solution comprises adding an accessory material to a pH-sensitive enteric material to form a polymer mixture. The accessory material has both film-forming and plasticizing properties together with the ability to render the enteric material permeable to drugs. This latter requirement may be satisfied if the accessory material is water soluble or has dialytic properties in its own right.

The dual mechanism polymer mixtures depend for their pH sensitivity on the usual enteric coating materials well known in the industry such as, but not limited to, cellulose acetate phthalate, polyvinylacetate phthalate, hydroxypropyl methylcellulose phthalate and methacrylic acid-methacrylic acid methyl ester copolymers. These materials may be used either individually or in combination. All of these materials require the addition of plasticizers to insure freedom from cracking due to stress, low temperature, low humidity and other less well understood causes.

A variety of plasticizers are available but many are not useful for the present invention. Some of the plasticizers available are water soluble, such as the polyethylene glycols or propylene glycol. Others have limited water solubility, such as triacetin. Still others, such a dibutylsebacate or diethyl phthalate, are quite insoluble. However, none of these plasticizers is a film-forming material in its own right and its addition to the basic pH-sensitive film-forming material will produce a weakened film or a film unable to act as a dialytic membrane. Instead, to prepare a dual mechanism polymer mixture having properties previously described, an accessory material must be added which can simultaneously act as a plasticizer, be a film-former in its own right, and render the enteric material permeable to drugs. There are further advantages for processing if the accessory material is also soluble in the same organic solvents in which the pH-sensitive materials are soluble.

Materials presently available in pharmaceutically acceptable grades which meet all of the necessary requirements include hydroxypropyl cellulose and hydroxyethyl cellulose. The former is both water and solvent soluble, the latter is water soluble but not soluble in any of the solvents commonly used for the enteric materials. Both are film-formers themselves and do not weaken the enteric films but actually strengthen them. Also, both act as plasticizers. Since these materials are water soluble they make the enteric materials permeable so that the composition as a whole can act as a release-rate controlling membrane by a dialytic process.

Both the hydroxypropyl and hydroxyethyl cellulose compounds are commercially available in a number of viscosity grades. While there is no special requirement for viscosity as far as their ultimate effect is concerned, the lower viscosity grades are more convenient to use. Higher concentrations, hence lower volumes, are more easily sprayed and solutions are more easily prepared.

These accessory materials are not generally recognized or used as plasticizers. Indeed, for some of their own individual applications, plasticizers may be required. However, both form films which are inherently flexible as shown by their resistance to the standard (MIT) flexing test, and show considerable strength and elongation before failure when subjected to tensile stress tests. When added to the previously mentioned enteric coating materials in proper quantity they impart enough of their own flexibility and resistance to cracking to confer on the enteric coating materials sufficient resistance to mechanical failure to function as plasticizers.

Applicant has also discovered that shellac may be employed as part or all of the accessory material and also constitute a minor portion of the synthetic enteric film former. More particularly, Applicant has discovered that small amounts of shellac, e.g., 10% added to the newer synthetic materials will produce systems which have dual mechanism characteristics. Even though shellac is not water soluble, films of it are water permeable, and the addition of minor amounts of shellac to the synthetic enteric film-formers referred to above makes these materials permeable to water and, hence, useful in the diffusion/disintegration dual mechanism system. Shellac being a film-former itself does not weaken the enteric film-former, and since it is a plasticizer as well, it overcomes the brittleness of the resultant film. When used as a minor component, shellac does not significantly modify the pH sensitivity characteristics of the synthetic enteric film-formers. However, when the shellac becomes a major component, e.g., 66% of the film-forming material, the system ceases to function in the dual mechanism mode.

The operative dual mechanism polymer mixture system disclosed herein normally comprises three parts. However, not all three parts are necessary for the system to function. The innermost part is a nucleus of a pharmaceutically neutral material, such as nonpareil seeds. This part is optional, but serves as a framework or base upon which the system may be built. A second layer consists of matrix or polymer mixture impregnated with drug. This layer is essential as it is the element possessing the dual mechanism characteristics. An overlying coating or envelope covering the first two parts comprises the third part and it, too, is optional. It may comprise the same or another dual mechanism polymer mixture and may itself be impregnated with a drug. The combination of the permeability of the outer coating or envelope and that of the underlying matrix or polymer mixture control the diffusion rate of the system.

What has been developed is a novel composition of film-forming materials, suitable for pharmaceutical use, which has hybrid properties, that is, dialytic properties in acidic media where the drug is in soluble form. Release will then take place by diffusion. When, however, the pH rises and the drug reverts to a less soluble form, the dialytic membrane dissolves or disintegrates and then releases the drug by a pH actuated mechanism.

This new technology has opened the way to an improved controlled release dosage form for drugs which have up until now presented formulators with the unusual problem of dealing with therapeutic agents whose water solubility falls markedly with rising pH as they move down the gastrointestinal tract. That is, their water solubility falls to levels too low to be useful in a pure diffusion rate controlled system.

The two rate controlling mechanisms, diffusion and disintegration, can each be adjusted and optimized independently of the other. The permeability of the membrane during the diffusion phase may be optimized as required by the ionic mobility of the drug. Similarly the pH at which the disintegration phase of release takes over, i.e., nominally about pH 5.0 or higher, may also be optimized as required by the pKa of the drug.

There are two fundamental differences between the release pattern that results from a simple enteric coated tablet and that which results during the disintegration phase of the new dual mechanism controlled release dosage form.

The prior art tablet is an "all or nothing" device. No drug at all is available from the tablet until the enteric coating disintegrates. All of the drug then becomes available in a very short period of time. Such a process is not optimum for a controlled release formulation where a gradual release over a period of hours is required. This aspect of the problem is partially but inadequately solved merely by the fact that the drug is contained in a multiplicity of discrete pellets which scatter in the gastrointestinal tract so that not all of them are subjected at any given time to a pH that will cause them to disintegrate.

A second more important difference, is that even in the absence of the scattering phenomenon described, these new dual mechanism polymer mixtures allow the drug content of the pellets to release gradually even when subjected to pH values that are substantially in excess of the minimum pH value necessary to initiate the disintegration mechanism.

B. Processing of the Dual Mechanism Polymer Mixture

Matrices and coatings of dual mechanism polymer mixture materials are produced by mixing an organic solution or aqueous dispersion of the appropriate polymer mixture materials. This mixture is used as a coating. The process may be carried out with equipment well known in the industry such as "pour on" or spray in the usual coating pans or spray application in a Glatt fluid bed, or a Wurster column or similar equipment. When aqueous dispersions of enteric coating materials are used, hydroxypropyl cellulose, hydroxyethyl cellulose or mixtures thereof may be the accessory material added. When organic solvents are used the accessory material is hydroxypropyl cellulose or shellac or both.

There are a number of modifications in the application of the dual mechanism polymer mixtures which can be made to adapt the process to meet the varying needs of drugs having different pKa values. Some of the enteric component materials will disintegrate at pH values as low as nominally about 5.0, others as high as 7.5. It may be necessary for part of some drugs to be applied to the nucleus during pellet formation with a higher pH disintegrating component material and the balance of the drug with one or more lower pH disintegrating component materials.

The relationship between in vitro release rates and in vivo performance at present is not sufficiently well understood to be able to predict, or fix a priori, in vitro specifications with adequate assurance or precision. But after an experimental batch is made and its bioavailability is determined, it will be readily apparent what modifications are necessary. The system is flexible and the release rate of either or both mechanisms can be adjusted once an initial bioavailability is determined and the direction of the change to be made, if any, is ascertained.

The application of free, unretarded drug as an immediately available top layer is also possible with these pellets. This is a common and well-known practice. The layer may be composed either of the same drug as that in the pellet or some other useful drug for which controlled release is not required.

C. Examples

The following are examples of the practice of this invention on a laboratory scale. All of them illustrate the initial steps necessary to adapt the new dual mechanism polymer mixture technology to a given therapeutic agent.

Once these item-specific details are worked out and the correlation between the in vitro dissolution and the bioavailability is determined, the process can readily be scaled up to commercial size batches in larger coating pans of hundreds of kilos capacity. It is only necessary to use spray equipment of greater delivery capacity and, preferably, mechanized calibrated drug powder metering machines. For this large scale operation it is possible to operate the spray and powder feed devices simultaneously and continuously with balanced warm air feed and exhaust as is already well known to persons skilled in the art.

Similarly, the development-size batches, descriptions of which follow, could alternatively be both developed and scaled up to commercial size in fluid bed type equipment (Wurster, Glatt, etc.) or some of the newer type coating pans such as the Accela or Driam equipment.

It would also be possible to form the drug into pellets with spheronizing equipment such as the Freund or Marumerizer or similar units. In this event the use of the nonpareil starting nucleii may be eliminated. The pellets of drug/polymer matrix may be coated with more of the pH sensitive dialytic polymer mixture material for further dissolution retardation control by any of the other devices previously referred to.

The arrangement of equipment, exhaust and warm air in all of the following examples is entirely standard and well known in the art. Also, in each of the examples the solution batch sizes shown are merely a matter of convenience and are not necessarily the amount required for the controlled release batch size illustrated.

EXAMPLE I—QUINIDINE GLUCONATE CONTROLLED RELEASE PELLETS

One thousand grams of nonpareil seeds, 25/30 mesh, were placed in a 50 cm diameter coating pan which was rotated at about 30 r.p.m. This pellet bed was wet with 30 gms of a polymer solution. The polymer solution was composed, by weight, of 13.5% methacrylic acid copolymer, NF XVII type A; 1.5% shellac NF XVII; and 85% isopropyl alcohol. The amount of solution sprayed was measured by timing the duration of a calibrated spray unit. Fifty grams of quinidine gluconate in fine powder form was added to the rotating pan over a period of about ½ minute. To dry the pellets and remove the solvent fumes a warm-air feed and exhaust were applied. The pellets dried and were free flowing in about 2 minutes.

This process, beginning with the spraying of the polymer solution, was continued until a total of 2000 gms of quinidine gluconate were added. Then the pellets were allowed to dry by applying the warm-air and exhaust to the rotating pan for about ½ hour. This yielded about 3 kg of pellets.

The pellets in the rotating pan were next sprayed with 50 gms of the polymer solution. Thirty grams of talc were then added to the rotating pellet bed over a ½ minute interval. The pellets were dried and the solvent fumes removed by application of the warm-air and exhaust for about 2 minutes.

This process was repeated until 450 gms talc was added. This is about 15% of the weight of the pellets before addition of talc.

Samples of the pellets during the last four additions of talc were taken and allowed to dry overnight in an open dish at 35° to 40° C. They were then assayed for dissolution using the NF XIV rotating bottle apparatus. The amount of drug released over time at various pH levels was measured. The results are shown in FIG. 1.

EXAMPLE II—DIPYRIDAMOLE CONTROLLED RELEASE PELLETS

Three thousand grams of nonpareil seeds, 25/30 mesh, were placed in a 50 cm diameter coating pan which was rotated at about 30 r.p.m. This pellet bed was wet with 30 gms of polymer solution. The polymer solution was composed, by weight, of 12.5% hydroxypropyl methylcellulose phthalate 220824 NF XVII; 1.25% hydroxypropyl cellulose NF XVII; and 86.25% of a 70% isopropyl alcohol 30% water mixture. The amount of polymer solution was measured by timing the duration of a calibrated spray unit. Fifty grams of dipyridamole in fine powder form was added to the rotating pan over a period of about ½ minute. To dry the pellets and remove the solvent fumes a warm-air feed and exhaust were applied. The pellets dried and were free flowing in about 2 minutes.

This process, beginning with the spraying of the polymer solution, was continued until a total of 3750 gms of dipyridamole were added.

Then the pellets were allowed to dry by applying the warm-air and exhaust to the rotating pan for about ½ hour. This yielded about 6.5 kg of pellets.

The pellets in the rotating pan were next sprayed with 50 gms of the polymer solution. Sixty grams of talc were then added to the rotating pellet bed over a ½ minute interval. The pellets were dried and the solvent fumes removed by application of the warm-air and exhaust for about 2 minutes.

This process was repeated until 3600 gms talc was added. This is about 55% of the weight of the pellets before addition of talc.

A sample of the pellets after the last addition of talc was taken and allowed to dry overnight in an open dish at 35° to 40° C. They were then assayed for dissolution using the NF rotating bottle apparatus. The amount of drug released over time at various pH levels was measured. The results are shown in FIG. 2.

EXAMPLE III—CHLORPROMAZINE HCl CONTROLLED RELEASE PELLETS

One thousand grams of nonpareil seeds, 25/30 mesh, were placed in a 50 cm diameter coating pan which was rotated at about 30 r.p.m. This pellet bed was wet with 50 gms of a polymer aqueous dispersion. The polymer aqueous dispersion was composed, by weight, of 1% hydroxyethyl cellulose NF XVII; 32% water; 67% methacrylic acid copolymer type C NF XVII 30% water aqueous dispersion. The hydroxyethyl cellulose must first be dissolved in water before adding the methacrylic copolymer aqueous dispersion. The amount of dispersion sprayed was measured by timing the duration of a calibrated spray unit. One hundred grams of chlorpromazine HCl in fine powder form was added to the rotating pan over a period of about ½ minute. To dry the pellets a warm-air feed and exhaust were used. The pellets dried and were free flowing in about 2 minutes.

This process, beginning with the spraying of the polymer dispersion, was continued until a total of 1000 gms of chlorpromazine HCl was added. Then the pellets were allowed to dry by applying the warm-air and exhaust to the rotating pan for about ½ hour. This yielded about 2.0 kg of pellets.

The pellets in the rotating pan were next sprayed with 50 gms of the polymer dispersion. Fifty grams of talc were then added to the rotating pellet over a ½ minute interval. The pellets were dried by application of the warm-air and exhaust for about 2 minutes.

This process was repeated until 200 gms talc was added. This is about 10% of the weight of the pellets before addition of talc.

A sample of the pellets taken after the last addition of talc was allowed to dry overnight in an open dish at 30° to 40° C. It was then assayed for dissolution using the NF rotating bottle apparatus. The amount of drug released over time at various pH levels were measured. The results are shown in FIG. 3.

What is claimed is:

1. An oral dosage form comprising at least one pellet prepared from a delivery system for a pharmaceutical drug of pH-dependent solubility, said delivery system consisting essentially of a pH-sensitive film forming coating composition, said coating composition consisting essentially of:
   A. a pH-sensitive enteric coating material selected from the group consisting of cellulose acetate phthalate, polyvinyl acetate phthalate, hydroxypropyl methylcellulose phthalate, methacrylic acid copolymers, and mixtures, in an amount of up about 95% by weight; and
   B. an accessory film forming coating material having the properties of being a film former in its own right, acting as a plasticizer to said enteric coating material, and rendering said enteric coating material permeable to said pharmaceutical drug, said accessory coating material selected from the group consisting of hydroxyethyl cellulose, hydroxypropyl cellulose, shellac, and mixtures, capable of plasticizing and conferring permeability to said enteric coating material, said accessory coating material present in an amount less than that of said enteric coating material;

C. wherein said accessory coating material modifies the properties of said enteric coating material, so that said enteric coating material forms a coating that is plasticized and does not exhibit embrittlement, and that functions as a pH-dependent dialytic membrane with controlled permeability for the gradual release of said pharmaceutical drug by diffusion at pH values at which the drug is water soluble, while at the same time possessing the ability of an enteric coating to release said pharmaceutical drug by disintegration at higher pH values when the drug becomes inadequately soluble to release by diffusion; and D. wherein said coating composition dispenses said pharmaceutical drug in metered fashion when said pH is below about 5.0, and acts as a pH sensor and promotes the complete release of said pharmaceutical drug by disintegration when said pH rises above about 5.0.

2. The oral dosage form of claim 1 wherein said pharmaceutical drug is initially water soluble and said coating composition is adapted to release water soluble pharmaceutical drugs contained therein by diffusion when exposed to aqueous conditions below a first pH of about 5.0, and is adapted to release said pharmaceutical drugs by disintegration in aqueous conditions at or above said first pH level.

3. The oral dosage form of claim 1 wherein said accessory coating material is present in an amount of up to about 10% by weight.

4. The oral dosage form of claim 1 wherein said accessory coating material is present in an amount of from about 5% to about 10% by weight.

5. The oral dosage form of claim 1 wherein said enteric coating material is present in an amount of from about 90% to about 95% by weight.

6. The oral dosage form of claim 1 wherein said enteric coating material comprises a methacrylic acid ester and said accessory coating material comprises shellac.

7. The oral dosage form of claim 1 wherein said enteric coating material comprises hydroxypropylmethyl cellulose phthalate, and said accessory coating material comprises hydroxypropyl cellulose.

8. The oral dosage form of claim 1 wherein said enteric coating material comprises a methacrylic acid copolymer and said accessory coating material comprises hydroxyethyl cellulose.

9. The oral dosage form of either of claims 6 or 7 wherein said enteric coating material is present in an amount of about 90% by weight, and said accessory coating material is present in an amount of about 10% by weight.

10. The oral dosage form of claim 9 wherein said enteric coating material is present in an amount of about 95% by weight, and said accessory coating material is present in an amount of about 5% by weight.

11. An oral dosage form comprising at least one pellet prepared from a pharmaceutical composition for the controlledrelease delivery of a pharmaceutical drug of pH-dependent variable solubility, said pharmaceutical composition consisting essentially of:

A. A pH-dependent film forming coating composition, said coating composition consisting essentially of:
  i. a pH-sensitive enteric coating material selected from the group consisting of cellulose acetate phthalate, polyvinyl acetate phthalate, hydroxypropyl methylcellulose phthalate, methacrylic acid copolymers, and mixtures, in an amount of up about 95% by weight; and
  ii. an accessory film forming coating material having the properties of being a film former in its own right, acting as a platicizer to said enteric coating material, and rendering said enteric coating material permeable to said pharmaceutical drug, said accessory coating material selected from the group consisting of hydroxyethyl cellulose, hydroxypropyl cellulose, shellac, and mixtures, capable of plasticizing and conferring permeability to said enteric coating material, said accessory coating material present in an amount less than that of said enteric coating material;
  iii. wherein said accessory coating material modifies the properties of said enteric coating material, so that said enteric coating material forms a coating that is plasticized and does not exhibit embrittlement, and that functions as a pH-dependent dialytic membrane with controlled permeability for the gradual release of said pharmaceutical drug by diffusion at pH values at which the drug is water soluble, while at the same time possessing the ability of an enteric coating to release said pharmaceutical drug by disintegration at higher pH values when the drug becomes inadequately soluble to release by diffusion; and
  iv. wherein said coating-composition dispenses said pharmaceutical drug in metered fashion when said pH is below about 5.0, and acts as a pH sensor and promotes the complete release of said pharmaceutical drug when said pH rises above about 5.0; and B. A pharmaceutical drug having pH-dependent solubility impregnated therein.

12. The oral dosage form of claim 11 wherein said pharmaceutical drug is water soluble and said coating composition is adapted to release water soluble pharmaceutical drugs contained therein by diffusion when exposed to aqueous conditions below a first pH of about 5.0, and is adapted to release said pharmaceutical drugs by disintegration in aqueous conditions at or above said first pH level.

13. The oral dosage form of claim 11 wherein said accessory coating material is present in an amount of up to about 10% by weight.

14. The oral dosage form of claim 11 wherein said accessory coating material is present in an amount of from about 5% to about 10% by weight.

15. The oral dosage form of claim 11 wherein said enteric coating material is present in an amount of from about 90% to about 95% by weight.

16. The oral dosage form of claim 11 wherein said enteric coating material comprises a methacrylic acid ester and said accessory coating material comprises shellac.

17. The oral dosage form of claim 11 wherein said enteric coating material comprises hydroxypropylmethyl cellulose phthalate, and said accessory coating material comprises hydroxypropyl cellulose.

18. The oral dosage form of claim 11 wherien said enteric coating material comprises a methacrylic acid copolymer and said accessory coating material comprises hydroxyethyl cellulose.

19. The oral dosage form of either of claims 16 or 17 wherein said enteric coating material is present in an amount of about 90% by weight, and said accessory coating material is present in an amount of about 10% by weight.

20. The oral dosage form of claim 19 wherein said enteric coating material is present in an amount of about 95% by weight, and said accessory coating material is present in an amount of about 5% by weight.

21. The oral dosage form of claim 11 wherein said pharmaceutical composition is prepared into tablet form.

22. The oral dosage form of claim 11 wherein said pharmaceutical composition is prepared as a plurality of pellets and is filled into a capsule.

23. The oral dosage form of claim 11 wherein said pellet is further coated with at least one layer of said pH-dependent film forming coating composition.

24. The oral dosage form of claim 11 wherein said pellet is further coated with at least one layer of said pharmaceutical composition.

25. The oral dosage form of claim 24 wherein the pharmaceutical drug impregnated into the at least one layer of said pharmaceutical composition is other than the pharmaceutical drug impregnated into said pellet.

* * * * *